United States Patent [19]
Winkler et al.

[11] Patent Number: 5,112,323
[45] Date of Patent: May 12, 1992

[54] WOUND EVACUATOR

[75] Inventors: Duane K. Winkler, Dover; Daniel H. Olson, Louisville, both of Ohio

[73] Assignee: Snyder Laboratories, Inc., Dover, Ohio

[21] Appl. No.: 476,844

[22] Filed: Feb. 8, 1990

[51] Int. Cl.⁵ .............................................. A61M 1/00
[52] U.S. Cl. ................................... 604/319; 604/133
[58] Field of Search ............... 604/319, 133, 132, 142

[56] References Cited
U.S. PATENT DOCUMENTS
4,664,652  5/1987  Weilbacher .................. 604/133

Primary Examiner—Randy C. Shay
Assistant Examiner—G. Gualtieri
Attorney, Agent, or Firm—Paul David Schoenle

[57] ABSTRACT

A wound evacuator is provided with a discharge valve assembly which permits body fluid contained within the wound evacuator to be drained to a collection bag. The discharge valve assembly is also designed to minimize leakage of body fluid when the collection bag is separated from the wound evacuator.

1 Claim, 2 Drawing Sheets

WOUND EVACUATOR

BACKGROUND OF THE INVENTION

The present invention relates to a wound evacuator for a patient to collect body fluids from the patient following surgery. In surgery, tissue is traumatized so that inflammation and bleeding result. In order to alleviate these conditions, a drainage tube is placed within the patient at the wound site and an evacuator in communication with the drainage tube is depressurized to suck body fluids away from the wound site.

In U.S. Pat. No. 4,664,652 (Weilbacher) a wound evacuator includes an inlet port and a discharge port. The inlet port is provided with a one-way check valve while the discharge port is open to receive a plug. To empty the evacuator, the end walls are squeezed together to force body fluids contained within the evacuator outwardly through the discharge port to a container or the like.

In U.S. Pat. No. 4,055,179 (Manschat et al) a urinary drainage container includes inlet and outlet tubes with a sleeve check valve on the outlet tube to control fluid discharge from the container.

In U.S. Pat. No. 3,900,029 (Melnick et al) a surgical evacuator includes a splash guard to control discharge of body fluids from the evacuator and a magnetized check valve is biased to a closed position to eliminate back flow of body fluids into the evacuator.

In U.S. Pat. No. 3,742,952 (Magers et al) a plug assembly cooperates with an inlet/outlet port to control fluid communication of body fluids through the port.

In U.S. Pat. No. 3,572,340 (Lloyd et al) a suction drainage device includes inlet and outlet tubes with a ball check valve preventing discharge of body fluids through the inlet tube.

With all of the above prior art devices the drainage of body fluids from the evacuator may result in some leakage of body fluids from an exhaust port following communication of the body fluids to a storage container. With infectious body fluids it is important to minimize human contact with the body fluids.

SUMMARY OF THE INVENTION

The present invention provides a wound evacuator which is easy to drain to a collection bag by means of a discharge valve assembly. The discharge valve assembly is orientated for easy connection with the collection bag and a valve member within the discharge valve assembly cooperates with a valve within the collection bag to substantially reduce leakage of body fluids upon emptying the wound evacuator.

It is an object of the present invention to provide a wound evacuator which is easily handled by an operator with minimal chance of body contact with the body fluids collected an discharged from the wound evacuator.

BRIEF DESCRIPTION OF THE PREFERRED EMBODIMENT

Figure 1:
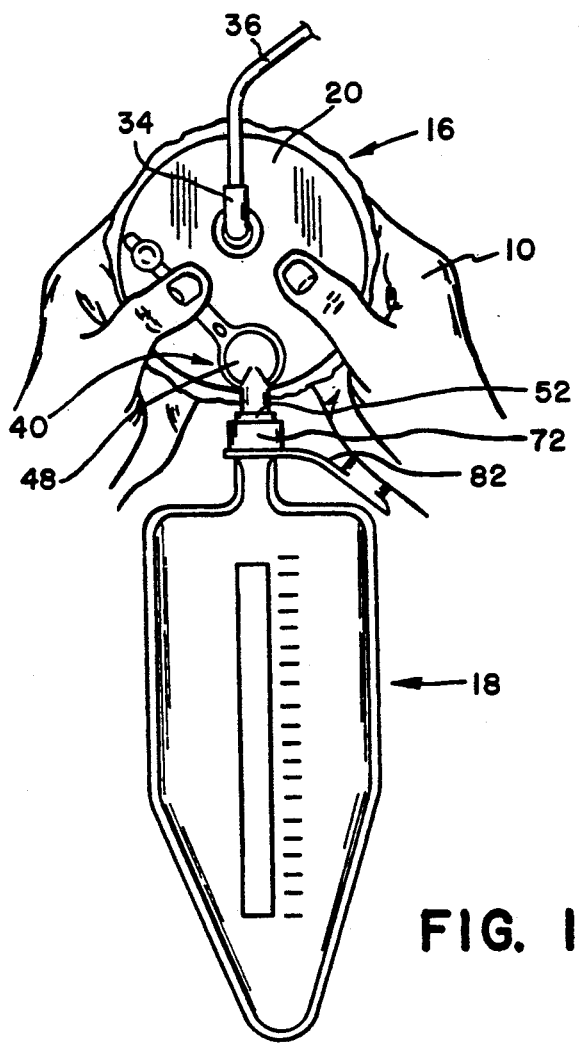
FIG. 1 is an illustration of a wound evacuator according to the present invention being emptied into a collection bag by an operator.

In FIG. 1 an operator with hands 10 and 12 is squeezing a wound evacuator 16 to communicate body fluids to a collection bag 18. When the wound evacuator is completely collapsed, the operator has just transferred the body fluid to the collection bag 18 and recharged the wound evacuator 16 simultaneously. The operator now has three options: 1) leave the collection bag attached for subsequent transferal of additional body fluid into the same bag, 2) remove the collection bag and replace it with another or, 3) remove the collection bag and close off the end fitting 52 with the spout cap 80. At this time, the operator can estimate the volume of body fluid which may be drawn and choose the most viable of the three options listed.

Figure 2:
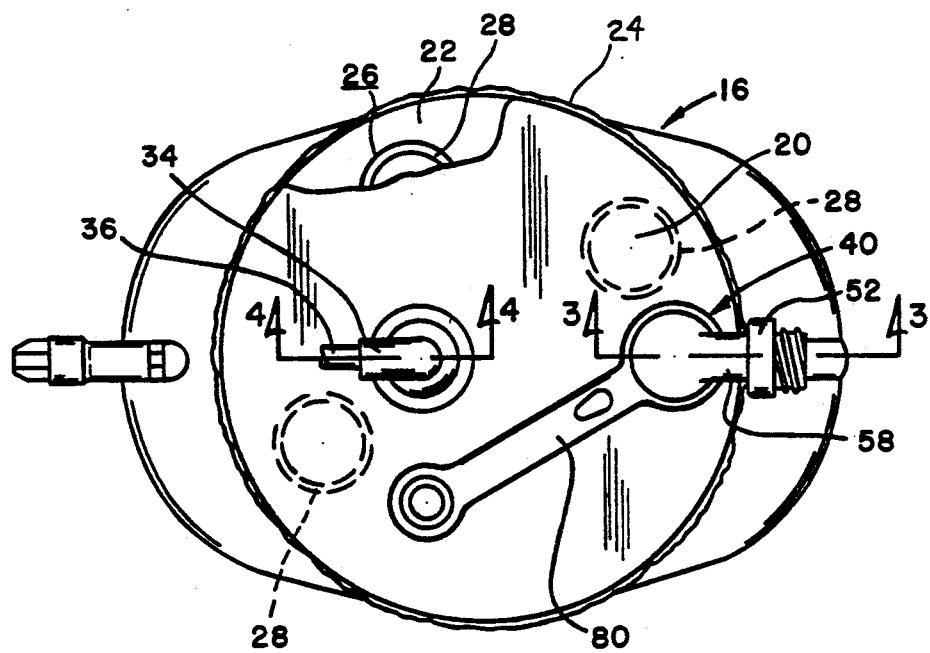
FIG. 2 is a top view of the wound evacuator.

Turning to FIG. 2 the wound evacuator 16 includes a pair of end walls 20 and 22 connected to a side wall 24 to substantially define a cylindrical cavity 26 with springs 28 grasping the end walls 20 and 22 away from each other. The construction of the walls, springs and cavity are substantially similar to that previously described in U.S. Pat. No. 4,664,652 issued to Eugene E. Weilbacher. On the end wall 20 an inlet opening 30 includes a one-way check valve 32 in the form of a flapper valve assembly. A fitting 34 connects the inlet opening 30 to a tube 36 extending from a wound site of a patient in a conventional manner. The inlet 30 is substantially disposed at the center of the end wall 20 while an outlet opening 38 (FIG. 3) receives a discharge valve assembly 40 near the edge of the end wall 20.

Figure 3:
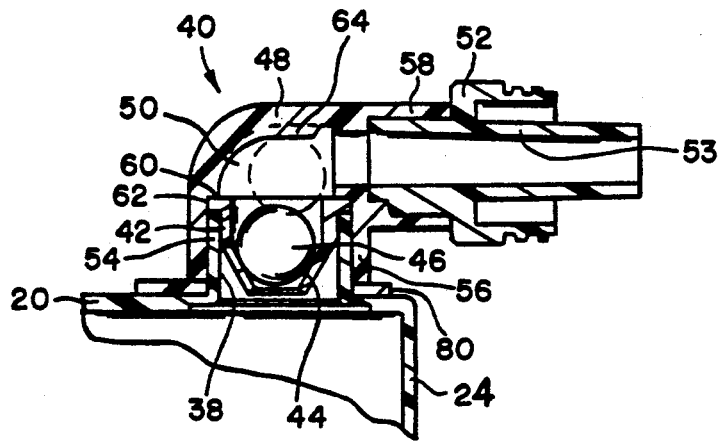
FIG. 3 is a cross-section view taken along line 3—3 of FIG. 2.
Figure 4:
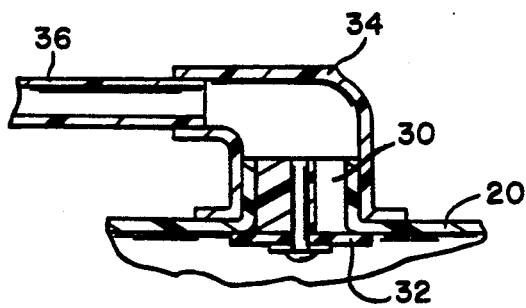
FIG. 4 is a cross-section view taken along line 4—4 of FIG. 2.

In FIG. 3 it is seen that the discharge valve assembly 40 includes a valve seat 42 with a frustoconical extension 44 disposed within the opening 38, a ball valve member 46 engageable with the valve seat 42, and a cap 48 forming a passage 50 leading from the opening 38 to an end fitting 52 with a bore 53 therethrough. The end wall 20 defines a cylindrical boss 54 to receive the valve seat 42. The cap 48 forms a first tubular end 56 fitting over the cylindrical boss 54 and a second tubular end 58 carrying the end fitting 52. The first tubular end 56 is perpendicular in orientation to the second tubular end 58 so that the end fitting 52 is carried outside a projection of the end wall 20 and offset from the side wall 24 as shown in FIGS. 2 and 3. A shoulder 60 on the first tubular end 56 opposes the end of the cylindrical boss 54 to capture a flange 62 of the valve seat against the end of the cylindrical boss 54. The cap 48 forms a thin ridge 64 extending into the passage 50 directly opposite the valve member 46 for a purpose to be explained hereinafter.

Figure 5:
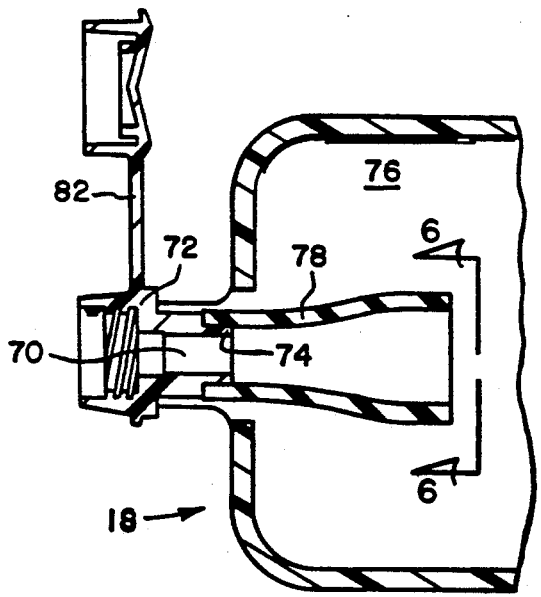
FIG. 5 is a cross-section of a valve assembly within the collection bag.
Figure 6:
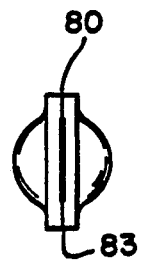
FIG. 6 is an end view of the collection bag valve assembly as indicated at 6—6 in FIG. 5.

Turning to FIGS. 1, 5 and 6, the collection bag 18 forms an end fitting 52. The spout 72 includes a projection 74 extending into a fluid chamber 76 to carry an anti-reflex valve 78. The material that are secured together at their longitudinal ends at 80 and 83 in FIG. 6. Before the anti-reflex valve is attached to the projection 74 the sheets of flexible material are flat in a relaxed mode. When attached to the projection 74, the anti-reflex valve 78 permits fluid flow from the inlet port 70 into the chamber 76 but prevents fluid flow in the reverse direction.

In order to utilize the wound evacuator 16 the tubing 36, which has previously been disposed within a patient wound site, is connected to the fitting 34. The operator uses his hands 10 and 12 to collapse the end walls 20 and 22. With the springs 28 in a contracted condition a separation force is exerted against the end walls 20 and 22 to expand the cavity 26 and create a vacuum therein. Such vacuum creates a pressure differential between the inside cavity 26 and the exterior environment to move the valve member 46 into sealing engagement with the frustoconical extension 44 of valve seat 42. The vacuum simultaneously pulls the flexible flapper valve 32 away from the end wall 20 to open tubing 36 to the vacuum within the cavity 26. As a result vacuum pulls body fluid from the patient in response to the force exerted by the springs 28 against the end walls 20 and 22. As body fluid is communicated into the cavity 26, the end walls 20 and 22 move away from each other to fill up the cavity with body fluid.

When the wound evacuator is to be drained, the collection bag 18 is connected to the wound evacuator 16 with spout 72 threadably coupled to the end fitting 52. As shown in FIG. 1, this connection is easily accomplished because the end fitting extends away from the end wall 20. Moreover, the end fitting extends in an opposite direction from the tubing 36 so that the collection bag 18 can be disposed below the wound evacuator 16 with the tubing above the wound evacuator 16. The operator grabs the wound evacuator 16 and squeezes the end walls 20 and 22 together as shown in FIG. 1. The end walls 20 and 22 collapse and generate fluid pressure within the body fluid contained within cavity 22 and force valve 32 to close while opening valve member 46. Body fluid is communicated into the passage 50 and out bore 53 into chamber 76 via anti-reflex valve 78. When the wound evacuator is collapsed with substantially all of the body fluid communicated to the collection bag 18 the operator releases the end walls to collect further body fluids as a result of vacuum created in the cavity 26. However, the vacuum within the cavity 26 now extends from the anti-reflex valve 78 through bore 53 and passage 50 because the wound evacuator is held in the upright position as shown in FIG. 1 and the valve member is freely disposed against the ridge 64 away from valve seat 42. As the collection bag 18 is released from the end fitting, the vacuum within the cavity 26 will pull air from the outside as well as remaining body fluids from the bore 53 and passage 50 into the cavity 26. Therefore, upon separation of the collection bag 18 from the end fitting 52 very little, if any, body fluids will be leaked to the environment to protect the operator in the event the patient's body fluid include infectious diseases. Following internal release of the spout 72 from the end fitting the vacuum will bias the valve member 46 into ready engagement with the valve seat to retain the vacuum in the cavity 26 for continued collection of body fluids from the patient. Additional collection bags are also connected to the end fitting if necessary.

The cap 48 cooperates with the end wall 20 to retain a strap 80 with a plug at the end for closing the end fitting 52, and the spout 72 includes a strap 82 with a plug for closing the spout 72.

Additional modifications and or changes in the preferred embodiment illustrated are feasible by one skilled in the art and the claims herein are not limited to the specific design illustrated.

We claim:

1. A wound evacuator for extracting body fluids from a patient via tubing extending from the patient to the evacuator, the evacuator including end walls connected by a side wall to form a cavity for receiving the body fluids, means within the cavity biasing the end walls away from each other, one of the end walls including a first opening and a second opening, the first opening including a one-way check valve and communicating with the tubing to permit flow of body fluids into the cavity from the tubing and substantially prevent flow of body fluids from the cavity to the patient, the second opening including a discharge valve assembly with a cap coupled to the one end wall, the valve assembly further including a valve seat within the second opening and a valve member cooperating with the valve seat to selectively restrict fluid communication through the second opening into the cavity, the cap defining a passageway and carrying an end fitting remote from the one end wall and directed away from the one-way check valve, the end fitting defining a bore in communication with the passageway such that body fluids within the cavity are selectively communicated outwardly from the end fitting to a collection bas via the passageway and the bore, the valve member being free to move between the valve seat and the cap in the absence of any spring force such that the valve member moves away from the valve seat and into the passageway when the end walls are moved toward each other to transmit body fluids outwardly from the cavity via the second opening as the wound evacuator is disposed in an upright position with the collection bag disposed below the evacuator, the cap including a ridge engageable with the valve member when the latter is in the passageway to prevent the valve member from closing the end fitting bore and the valve member is pressure responsive to a vacuum within the cavity when the end walls are moving apart to move from the passageway to a sealing engagement with the valve seat, the cavity being expandable to receive body fluids which are initially pulled from the passageway and end fitting bore so that fluids are removed from the passageway and end fitting bore before the valve member is brought into sealing engagement with the valve seat, thereby reducing leakage from the end fitting bore and passageway, the one end wall further defining a boss extending outwardly to form the second opening, the cap including a first tubular end engageable with the boss and a second tubular end substantially perpendicular to the first tubular end for carrying the end fitting in a substantially perpendicular direction to the boss so that the second tubular end is pointed downwardly when the wound evacuator is disposed in the upright position, the first tubular end forming a shoulder facing the end of the boss and the valve seat including a flange secured between the shoulder and the end of the boss for positioning the valve member within the second opening.

* * * * *